United States Patent
Slater

(10) Patent No.: US 6,907,149 B2
(45) Date of Patent: Jun. 14, 2005

(54) COMPACT OPTICAL MEASUREMENT PROBE

(75) Inventor: Joseph B. Slater, Dexter, MI (US)

(73) Assignee: Kaiser Optical Systems, Inc., Ann Arbor, MI (US)

( * ) Notice: Subject to any disclaimer, the term of this patent is extended or adjusted under 35 U.S.C. 154(b) by 139 days.

(21) Appl. No.: 10/350,580

(22) Filed: Jan. 24, 2003

(65) Prior Publication Data

US 2003/0147593 A1 Aug. 7, 2003

Related U.S. Application Data

(60) Provisional application No. 60/353,330, filed on Feb. 1, 2002.

(51) Int. Cl.[7] .................................................. G02B 6/00
(52) U.S. Cl. ........................... 385/12; 385/31; 385/147; 250/227.11; 356/301; 356/318
(58) Field of Search .................................. 356/301, 318; 385/12, 31, 49, 50, 147; 250/227.11; 347/260; 372/20; 424/9.1; 600/160

(56) References Cited

U.S. PATENT DOCUMENTS

| | | | | | |
|---|---|---|---|---|---|
| 5,943,128 A | * | 8/1999 | Slater | .......................... | 356/301 |
| 6,037,968 A | * | 3/2000 | Emge et al. | ................. | 347/260 |
| 6,038,363 A | * | 3/2000 | Slater et al. | ................. | 385/147 |
| 6,364,829 B1 | * | 4/2002 | Fulghum | ..................... | 600/160 |
| 6,498,800 B1 | * | 12/2002 | Watterson et al. | ............. | 372/20 |
| 6,503,478 B2 | * | 1/2003 | Chaiken et al. | ............... | 424/9.1 |

\* cited by examiner

*Primary Examiner*—Frank G. Font
*Assistant Examiner*—Mary El-Shammaa
(74) *Attorney, Agent, or Firm*—Gifford, Krass, Groh, Sprinkle, Anderson & Citkowski, PC

(57) ABSTRACT

A remote optical measurement suitable for Raman and fluorescence detection uses one or more dielectric components and an optical configuration which affords significant miniaturization, in some cases resulting in a probe with dimensions on the order of one-half inch or less on a side. A primary application is the pharmaceutical market, wherein the reactors vessels are only 1-inch in diameter, causing a scale down of instrumentation due to space requirements.

5 Claims, 1 Drawing Sheet

COMPACT OPTICAL MEASUREMENT PROBE

REFERENCE TO RELATED APPLICATION

This application claims priority from U.S. Provisional Patent Application Ser. No. 60/353,330, filed Feb. 1, 2002, the entire content of which is incorporated herein by reference.

FIELD OF THE INVENTION

This invention relates generally to optical measurement probes and, in particular, to a probe that uses one or more dielectric components to reduce size.

BACKGROUND OF THE INVENTION

Induced radiative effects such as Raman scattering and fluorescence have become extremely valuable investigative tools. To characterize a composition in a remote or hostile environment, optical fibers may advantageously be used to deliver excitation energy to a sample under investigation and to carry scattered radiation back to means for spectral analysis. An excitation source path may take the form of a laser providing a stimulus at an appropriate wavelength coupled to an input fiber, and a collection path may be made up of a second fiber carrying return radiative information to a spectral analysis tool such as a spectrograph.

Such remote spectral analysis presents technical challenges, however, including the strong scattering signature of the material used for the optical fiber, this interference potentially being generated by both the laser excitation in the illumination fiber and any strong Rayleigh (unshifted) Scattering allowed to enter the collection fiber. These spurious fiber signatures can compete with, or even overshadow, the desired signature of the sample under test, particularly when long lengths of fiber are used.

In a typical arrangement, energy from an excitation laser is coupled into the illumination fiber. This stimulation begins as a relatively pure, single wavelength of light, but while traveling through the fiber, the laser energy induces Raman scattering within the fiber material, typically composed of silica, yielding a spectrum at the output of the illumination fiber which contains spurious Raman lines in addition to the laser wavelength.

Unless these undesired lines are eliminated from the illumination path before reaching the sample, their Rayleigh scatter at the sample may be indistinguishable from the true, shifted Raman scatter due to the laser excitation of the sample. Therefore, a laser band pass device is used to remove these unwanted wavelengths, thereby outputting, ideally, the single laser line to the illumination optic and sample under characterization. This assumes, of course, that the illumination optic contains a sufficiently short optical path that it does not itself generate significant spurious scattering.

The light scattered by the sample is collected by a collection optic, which may be the same element as the illumination optic used in counter-propagating fashion. At the output of the collection optic, the scattered radiation consists of the unshifted Rayleigh scatter at the laser wavelength and the shifted Raman scatter that characterizes the sample under test. Since the Rayleigh scatter is several orders of magnitude stronger than the Raman scatter, if allowed to enter collection fiber, this strong Rayleigh scatter can excite spurious Raman scattering within the collection fiber similar to this situation within illumination fiber.

This Rayleigh scatter must therefore be rejected before being coupled to collection fiber. This may be accomplished with a Rayleigh rejection element to remove the strong Rayleigh line. The collection fiber then conducts only the relatively weak Raman scattering lines from the sample to an analysis instrument such as a spectrograph for detection. Particularly in more modern instruments, holographic notch filters are used as narrowband reflective elements to reject the Rayleigh scatter.

SUMMARY OF THE INVENTION

Figure 1:
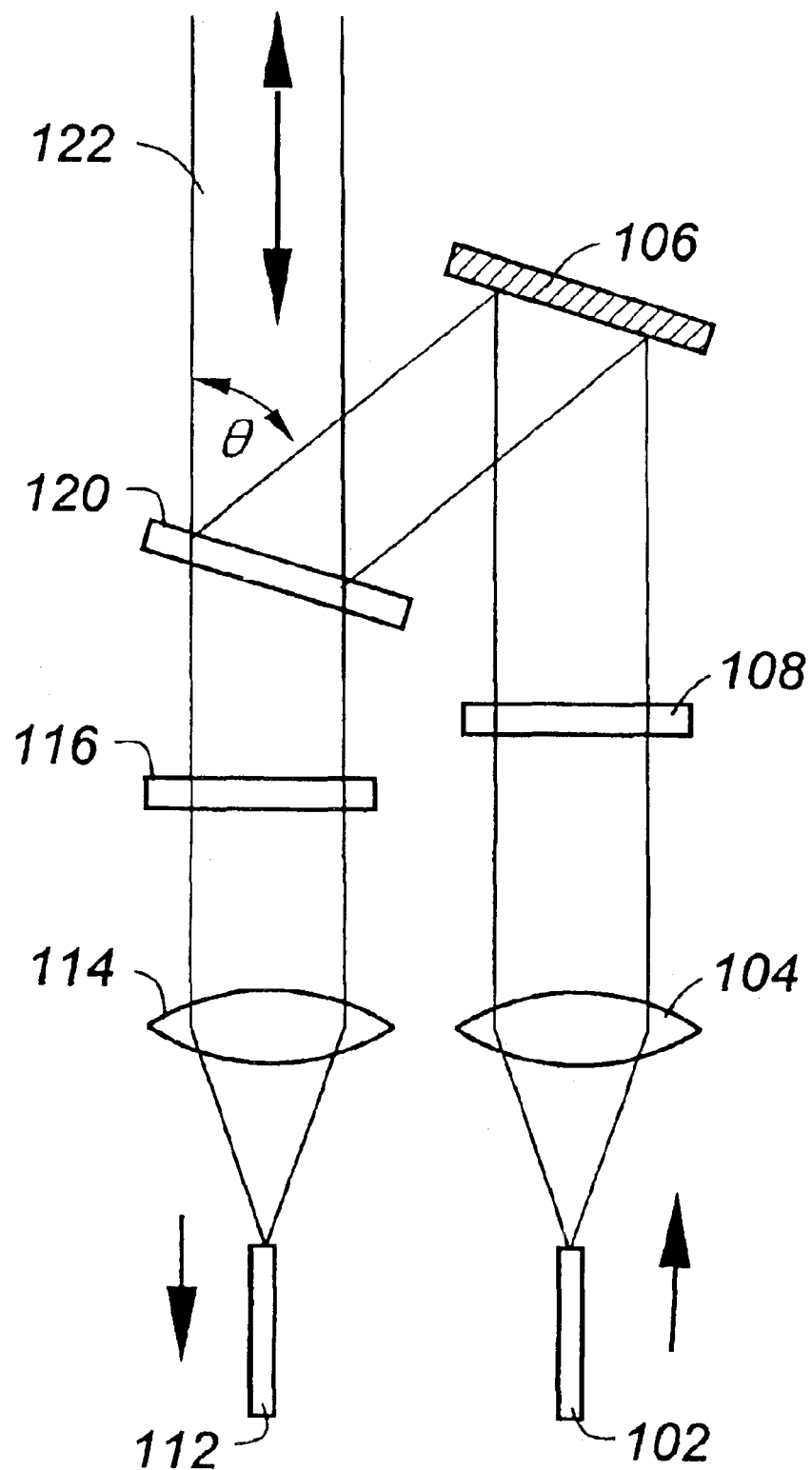
FIG. 1 is a diagram that depicts a preferred embodiment of the invention.

This invention resides in a remote optical measurement suitable for Raman and fluorescence detection, but which uses one or more dielectric components and an optical configuration which affords significant miniaturization, in some cases resulting in a probe with dimensions on the order of one-half inch or less on a side. A primary application is the pharmaceutical market, wherein the reactors vessels are only 1-inch in diameter, causing a scale down of instrumentation due to space requirements.

DETAILED DESCRIPTION OF THE INVENTION

FIG. 1 is a diagram which shows the preferred embodiment of the invention. Excitation illumination is brought into the probe over fiber 102, which is then collimated by lens 104. The collimated light then passes through a bandpass filter 108 to remove the non-laser wavelengths generated en route from the source. In contrast to previous designs, which rely exclusively on holographic optical elements, this invention uses a dielectric component, at least the bandpass filter 108, since this allows the element to be fabricated in a more compact size using existing technology. The filtered light is reflected by a mirror 106 onto a beam combiner 120 which is then directed to a sample along a counter-propagating path 122. The light scattered by the sample under investigation returns along path 122, passes through beam combiner 120, and is filtered by an optional notch filter 116 before being focused by lens 114 onto the end of collection fiber 112. Although the beam combiner 120 and optional notch filter 116 may be holographic elements, dielectric edge filters are used here instead as well for further compaction.

Note that although the mirror and combiner may be supported at different angles, including 45 degrees, the preferred embodiment uses a tilt of 20 degrees or less, not only for polarization insensitivity, but in addition, these smaller angles afford a compact configuration and optimal performance of transmission the collection in conjunction with rejection of the laser and Rayleigh scatter.

I claim:

1. A miniature fiber-optic probehead configured for interconnection to a first optical fiber for carrying excitation energy to the probehead, and a second optical fiber for carrying collected energy for analysis, the probehead comprising:
   a dielectric bandpass filter for filtering the excitation energy;
   a beam combiner for merging the filtered excitation energy into a combined, counter-propagating sample excitation and collection path; and
   wherein the beam combiner is tilted at an angle of less than 20 degrees relative to the combined, counter-propagating sample excitation and collection path.

2. The miniature fiber-optic probehead of claim 1, wherein the beam combiner is a dielectric edge filter.

3. The miniature fiber-optic probehead of claim 1, further including a notch filter for filtering the collected energy before entering the collection fiber.

4. The miniature fiber-optic probehead of claim 3, wherein the notch filter is a dielectric edge filter.

5. A miniature fiber-optic probehead configured for interconnection to a first optical fiber for carrying excitation energy to the probehead, and a second optical fiber for carrying collected energy for analysis, the probehead comprising:

a dielectric bandpass filter for filtering the excitation energy;

a dielectric beam combiner for merging the filtered excitation energy into a combined, counter-propagating sample excitation and collection path, the beam combiner being supported at an angle of less than 20 degrees relative to the combined, counter-propagating sample excitation and collection path; and a dielectric notch filter for filtering the collected energy before entering the collection fiber.

* * * * *